United States Patent
Ying et al.

(10) Patent No.: US 7,534,489 B2
(45) Date of Patent: May 19, 2009

(54) COATED COMPOSITES OF MAGNETIC MATERIAL AND QUANTUM DOTS

(75) Inventors: Jackie Y. Ying, Singapore (SG); Subramanian T. Selvan, Singapore (SG); Dong Kee Yi, Singapore (SG); Su Seong Lee, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 0 days.

(21) Appl. No.: 10/950,194

(22) Filed: Sep. 24, 2004

(65) Prior Publication Data

US 2006/0068203 A1 Mar. 30, 2006

(51) Int. Cl.
*B32B 5/66* (2006.01)

(52) U.S. Cl. .................. 428/402; 428/403; 428/404; 428/405; 428/406; 427/212; 427/213.3; 427/213.31; 427/219

(58) Field of Classification Search .................. 428/402, 428/403, 404; 427/212, 213.3, 213.31, 219
See application file for complete search history.

(56) References Cited

U.S. PATENT DOCUMENTS

| | | | |
|---|---|---|---|
| 4,751,194 A | 6/1988 | Cibert et al. |
| 5,549,973 A | 8/1996 | Majetich et al. |
| 5,751,018 A | 5/1998 | Alivisatos et al. |
| 5,783,263 A | 7/1998 | Majetich et al. |
| 5,788,738 A | 8/1998 | Pirzada et al. |
| 5,879,715 A | 3/1999 | Higgins et al. |
| 5,906,670 A | 5/1999 | Dobson et al. |
| 5,965,212 A | 10/1999 | Dobson et al. |
| 5,990,479 A | 11/1999 | Weiss et al. |
| 6,048,616 A | 4/2000 | Gallagher et al. |
| 6,090,666 A | 7/2000 | Ueda et al. |
| 6,103,868 A | 8/2000 | Heath et al. |
| 6,114,038 A | 9/2000 | Castro et al. |
| 6,179,912 B1 | 1/2001 | Barbera-Guillem et al. |
| 6,194,213 B1 | 2/2001 | Barbera-Guillem |
| 6,194,237 B1 | 2/2001 | Kim et al. |
| 6,203,768 B1 | 3/2001 | McCormick et al. |
| 6,207,229 B1 | 3/2001 | Bawendi et al. |
| 6,207,392 B1 | 3/2001 | Weiss et al. |
| 6,221,602 B1 | 4/2001 | Barbera-Guillem et al. |
| 6,225,198 B1 | 5/2001 | Alivisatos et al. |
| 6,251,303 B1 | 6/2001 | Bawendi et al. |
| 6,255,198 B1 | 7/2001 | Linthicum et al. |
| 6,262,129 B1 | 7/2001 | Murray et al. |
| 6,274,323 B1 | 8/2001 | Bruchez et al. |
| 6,306,610 B1 | 10/2001 | Bawendi et al. |
| 6,306,736 B1 | 10/2001 | Alivisatos et al. |
| 6,309,701 B1 | 10/2001 | Barbera-Guillem |
| 6,319,426 B1 | 11/2001 | Bawendi et al. |
| 6,319,607 B1 | 11/2001 | Barbera-Guillem et al. |
| 6,322,901 B1 | 11/2001 | Bawendi et al. |
| 6,379,635 B2 | 4/2002 | O'Brien et al. |
| 6,423,551 B1 | 7/2002 | Weiss et al. |
| 6,426,513 B1 | 7/2002 | Bawendi et al. |
| 6,440,213 B1 | 8/2002 | Alivisatos et al. |
| 6,444,143 B2 | 9/2002 | Bawendi et al. |
| 6,444,223 B1 | 9/2002 | Tracy et al. |
| 6,468,808 B1 | 10/2002 | Nie et al. |
| 6,548,264 B1 | 4/2003 | Tan et al. |
| 6,572,673 B2 | 6/2003 | Lee et al. |
| 6,576,155 B1 | 6/2003 | Barbera-Guillem |
| 6,576,291 B2 | 6/2003 | Bawendi et al. |
| 6,596,194 B1 | 7/2003 | Dobson et al. |
| 6,602,671 B1 | 8/2003 | Bawendi et al. |
| 6,607,829 B1 | 8/2003 | Bawendi et al. |
| 6,617,583 B1 | 9/2003 | Bawendi et al. |
| 6,623,559 B2 | 9/2003 | Huang |
| 6,630,307 B2 | 10/2003 | Bruchez et al. |
| 6,649,138 B2 | 11/2003 | Adams et al. |
| 6,676,729 B2 | 1/2004 | Sun |
| 6,680,211 B2 | 1/2004 | Barbera-Guillem et al. |
| 6,682,596 B2 | 1/2004 | Zehnder et al. |
| 6,690,059 B1 | 2/2004 | Lojek |
| 6,699,723 B1 | 3/2004 | Weiss et al. |
| 6,702,957 B2 | 3/2004 | Konrad et al. |
| 6,720,411 B2 | 4/2004 | Mirkin et al. |
| 2002/0164271 A1* | 11/2002 | Ho |
| 2003/0178309 A1* | 9/2003 | Huang et al. |
| 2003/0186522 A1 | 10/2003 | Duan et al. |
| 2004/0005723 A1 | 1/2004 | Empedodes et al. |
| 2004/0026684 A1 | 2/2004 | Empedodes |
| 2004/0086885 A1 | 5/2004 | Lee et al. |
| 2006/0053971 A1 | 3/2006 | Sun et al. |

FOREIGN PATENT DOCUMENTS

EP 0 949 302 A2 10/1999
WO WO 02/055186 A2 7/2002

OTHER PUBLICATIONS

International Search Report, from PCT/US2005/034241, dated Sep. 7, 2006.

(Continued)

*Primary Examiner*—Leszek Kiliman
(74) *Attorney, Agent, or Firm*—Wolf, Greenfield & Sacks, P.C.

(57) ABSTRACT

Composites and methods associated with the same are provided. The composite structures are formed of quantum dots and magnetic nanoparticles. The structures may be coated, for example, with a non-organic shell such as silica. In some cases, the shell may be functionalized or derivatized to include compounds, atoms, or materials that can alter or improve properties such as water solubility, water stability, photo-stability and biocompatibility. A reverse microemulsion process can be used to form the coated composites. The composition and other characteristics of the composites may be controlled to provide desired magnetic and optical properties. The structures may be used in a variety of applications including biological labeling, magnetic resonance imagine (MRI) and drug targeting, amongst others.

18 Claims, 4 Drawing Sheets

OTHER PUBLICATIONS

Alivisatos, "Perspectives on the Physical Chemistry of Semiconductor Nanocrystals," J. Phys. Chem. B 100:13226 (1996).

Bawendi et al., "Electronic Structure and Photoexcited-Carrier Dynamics in Nanometer-size CdSe Cluster," Phys. Rev. Lett. 65:1623 (1990).

Bowen Katari et al., "X-Ray Photoelectron Spectroscopy of CdSe Nanocrystals with Applications to Studies of the Nanocrystal Surface," J. Phys. Chem. 98:4109 (1994).

Bruchez, Jr. et al., "Semiconductor Nancrystals as Fluorescent Biological Labels," Science 281:2013 (1998).

Chan et al., "Size-Controlled Growth of CdSe Nanocrystals in Microfluidic Reactors" Nano Lett. 3(2):199 (2003).

Chang et al., "Preparation and Properties of Tailored Morphology, Monodisperse Colloidal Silica-Cadmium Sulfide Nanocomposites," J. Am. Chem. Soc. 116:6739 (1994).

Correa-Duarte et al., "Stabilization of CdS Semiconductor Nanoparticles Against Photodegradation by a Silica Coating Procedure," Chem. Phys. Lett. 286:497 (1998).

Cumberland et al., "Inorganic Clusters as Single Source Precursors for Preparation of CdSe, ZnSe, CdSe/ZnS Nanomaterials," Chem. Mater. 14, 1576 (2002).

Dabbousi et al., "(CdSe)ZnS Core-Shell Quantum Dots: Synthesis and Characterization of a Size Series of Highly Luminescent Nanocrystallites," J. Phys. Chem. B 101:9463 (1997).

Danek et al., "Synthesis of Luminescent Thin-Film CdSe/ZnSe Quantum Dot Composites Using CdSe Quantum Dots Passivated with an Overlayer of ZnSe," Chem. Mater. 8:173 (1996).

Dubertret et al., "In Vivo Imaging of Quantum Dots Encapsulated in Phospholipid Micelles," Science 298:1759 (2002).

Eychmuller, "Structure and Photophysics of Semiconductor Nanocrystals," J. Phys. Chem. B 104:6514 (2000).

Gaponik et al., "Thiol-Capping of CdTe Nanocrystals: An Alternative to Organometallic Synthetic Routes," J. Phys. Chem. B 106:7177 (2002).

Gerion et al., "Synthesis and Properties of Biocompatible Water-Soluable Silica-Coated CdSe/ZnS Semiconductor Quantum Dots," J. Phys. Chem. B 105:8861 (2001).

Gu, et al., "Facile One-Pot Synthesis of Bifunctional Heterodimers of Nanoparticles: A Conjugate of Quantum Dot and Magnetic Nanoparticles," J. Am. Chem. Soc. 126:5664 (2004).

Han et al., "Quantum-Dot-Tagged Microbeads for Multiplexed Optical Coding of Biomolecules," Nature Biotechnology 19:631 (2001).

Hines et al.; "Synthesis and Characterization of Strongly Luminescing ZnS-Capped CdSe Nanocrystals," J. Phys. Chem. 100:468 (1996).

Kim et al., "Type-II Quantum Dots: CdTe/CdSe(Core/Shell) and CdSe/ZnTe(Core/Shell) Heterostructures," J. Am. Chem. Soc. 125:11466 (2003).

Klarreich, "Biologists Join the Dots," Nature 413:450 (2001).

Lal et al., "Silica Nanobubbles Containing an Organic Dye in a Multilayered Organic/Inorganic Heterostructure with Enhanced Luminescence," Chem. Mater. 12:2632 (2000).

Leatherdale et al., "On the Absorbtion Cross Section of CdSe Nanocrystal Quantum Dots," J. Phys. Chem. B 106:7619 (2002).

Liz-Marzan et al., "Synthesis of Nanosized Gold-Silica Core-Shell Particles," Langmuir 12:4329 (1996).

Manna et al., "Synthesis of Soluble and Processable Rod-, Arrow-, Teardrop-, and Tetrapod-Shaped CdSe Nancrystals," J. Am. Chem. Soc. 122:12700 (2000).

Mattoussi et al., "Self-Assembly of CdSe-ZnS Quantum Dot Bioconjugates Using an Engineered Recombinant Protein," J. Am. Chem. Soc. 122, 12142 (2000).

Mulvaney et al., "Silica Encapsulation of Quantum Dots and Metal Clusters," J. Mater. Chem. 10:1259 (2000).

Murray et al., "Self-Organisation of CdSe Nanocrystallites into Three-Dimensional Quantum Dot Superlattices," Science 270:1335 (1995).

Murray et al., "Synthesis and Characterization of Nearly Monodisperse CdE (E=sulfur, selenium, tellurium) Semiconductor Nanocrystallites," J. Am. Chem. Soc. 115:8706 (1993).

Niemeyer, "Nanoparticles, Proteins, and Nucleic Acids: Biotechnology Meets Materials Science," Angew. Chem. Int. Ed. 40:4128 (2001).

Norris et al., "Measurement of the Size Dependent Hole Spectrum in CdSe Quantum Dots," Phys. Rev. Lett. 72:2612 (1994).

Pathak et al., "Hydrozylated Quantum Dots as Luminescent Probes for In Situ Hybridization" J. Am. Chem. Soc. 123:4103 (2001).

Peng et al., "Formation of High-Quality CdTe, CdSe, and CdS Nanocrystals Using CdO as Precursor," J. Am. Chem. Soc. 123:183 (2001).

Redi, et al., "Three-Dimensional Binary Superlattices of Magnetic Nanocrystals and Semiconductor Quantum Dots," Nature 423:968 (2003).

Rogach et al., "Raisin Bun-Type Composite Spheres of Silica and Semiconductor Nancrystals," Chem. Mater. 12:2676 (2000).

Schroedter et al., "Biofunctionalization of Silica-Coated CdTe and Gold Nanocrystals," Nano. Lett. 2(12):1363 (2002).

Selvan et al., "Fabrication of Inorganic Nanocomposites Using Self-Assembly and Sol-Gel Processing," in Nanoscale Materials, Kluwer Academic Publishers, 247-272 (2003).

Selvan et al., "Synthesis of Tunable, Highly Luminescent QD-Glasses Through Sol-Gel Processing," Adv. Mater. 13:985 (2001).

Sinani et al., "Collagen Coating Promotes Biocompatability of Semiconductor Nanoparticles in Stratified LBL Films," Nano. Lett. 3(9):1177 (2003).

Talapin et al., "Dynamic Distribution of Growth Rates within the Ensembles of Colloidal II-VI and III-V Semiconductor Nancrystals as a Factor Governing Their Photoluminescence Efficiency," J. Am. Chem. Soc. 124:5782 (2002).

Tian et al., "Coupled Composite CdS-CdSe and Core-Shell Types of (CdS)CdSe and (CdSe)CdS Nanoparticles," J. Phys. Chem. 100:8927 (1996).

Vestal, et al., "Synthesis and Magnetic Characterization of Mn and Co Spinel Ferrite-Silica Nanoparticles with Tunable Magnetic Core," Nano Lett. 3(12):1739 (2003).

Wang et al., "Photochemical Incorporation of Silver Quantum Dots in Monodisperse Silica Colloids for Photonic Crystal Applications," J. Am. Chem. Soc. 123:12528 (2001).

Wang et al., Superparamagnetic Fe2O3Beads—CdSe/ZnS Quantum Dots Core-Shell Nanocomposite Particles for Cell Separation, Nano Lett. 0(0):A-E (2004).

Hyeon, T., et al., "Synthesis of Highly Crystalline and Mondisperse Maghemite Nanocrystallites without a Size-Selection Process" J. Am. Chem. Soc. vol. 123, 12798-12801, 2001 (Published on web Nov. 29, 2001).

Lu, Y., et al., "Modifyinig the Surface Properties of Superparamagnetic Iron Oxide Nanoparticles through A Sol—Gel Approach", Nano Letters, 2002, vol. 2, No. 3, 183-186, 2002 (Published on web Jan. 11, 2002).

Wang, D., et al. "Superparamagnetic $Fe_2O_3$ Beads—CdSe/ZnS Quantum Dots Core—Shell Nanocomposite Particles for Cell Separation", Nano Letters, 2004, vol. 4, No. 3, 409-413, 2004 (Published on web Jan. 24, 2004).

Yang, H., et al., "Magnetic—Containing Spherical Silica Nanoparticles for Biocatalysis and Bioseperations", Anal. Chem. vol. 76, No. 5, 1316-1321, Mar. 1, 2004 (published on web Jan. 24, 2004).

* cited by examiner

COATED COMPOSITES OF MAGNETIC MATERIAL AND QUANTUM DOTS

BACKGROUND OF INVENTION

1. Field of the Invention

The invention relates generally to nano-size structures, and in particular, to coated composites of magnetic nanoparticles and quantum dots, as well as methods associated with the same.

2. Discussion of Related Art

Nanoparticles are microscopic particles of matter having dimensions on the nanometer scale (e.g., less than 100 nanometers). Of particular interest are a class of nanoparticles known as quantum dots, or semiconductor nanocrystals, that exhibit properties that make them particularly useful in a variety of applications including as fluorescent probes in biological labeling and diagnostics. Because of quantum confinement effects, quantum dots can exhibit size-dependent optical properties. For example, cadmium selenide (CdSe) quantum dots can emit across the entire visible spectrum when the size of the crystal is varied over the range of from two to six nanometers.

When quantum dots are irradiated, more energy is required to promote the electrons to a higher state, leading to an increase in energy release in the form of photons and light emission in a color that is characteristic of the material. The resulting photons that are released typically exhibit a shorter wavelength than those released from a bulk form of the same material. The quantum confinement of electrons and holes in three dimensions contributes to an increasing effective band gap with decreasing nanocrystal size. Therefore, smaller quantum dots typically exhibit shorter emitted photon wavelength.

Magnetic nanoparticles are another class of nanoparticles. These particles have also generated considerable interest because of their magnetic properties and small dimensions.

SUMMARY OF INVENTION

The invention is directed, in part, to composites of magnetic material (e.g., magnetic nanoparticles) and quantum dots, as well as methods associated with the same.

In one aspect, a composite is provided. The composite comprises at least one quantum dot and at least one magnetic material associated with the at least one quantum dot to form a core. A shell at least partially encapsulates the core.

In another aspect, a composite structure is provided. The composite structure comprises a plurality of quantum dots and at least one magnetic particle associated with the plurality of quantum dots to form a core. A silica shell at least partially encapsulates the core.

In another aspect, a method of making a composite is provided. The method comprises introducing magnetic nanoparticles and quantum dots to an aqueous-in-nonaqueous emulsion, and contacting the magnetic nanoparticles and quantum dots with a surfactant. The method further comprises forming a core comprising at least one magnetic nanoparticle and at least one quantum dot in an aqueous phase of the emulsion. The method further comprises introducing a shell precursor to the emulsion; and, polymerizing the precursor to form a shell that at least partially encapsulates the core to form a composite.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention relates to composites and methods associated with the same. The composite structures include quantum dots and magnetic material (e.g., magnetic nanoparticles). The structures may be coated, for example, with a shell such as silica. In some cases, the shell may be functionalized or derivatized to include compounds, atoms, or materials that can alter or improve properties such as water solubility, water stability, photo-stability and biocompatibility. A reverse microemulsion process can be used to form the coated composites. As described further below, the composition and other characteristics of the composites may be controlled to provide desired magnetic and optical properties. The structures may be used in a variety of applications including biological labeling, magnetic resonance imagine (MRI) and drug targeting, amongst others.

Figure 1:
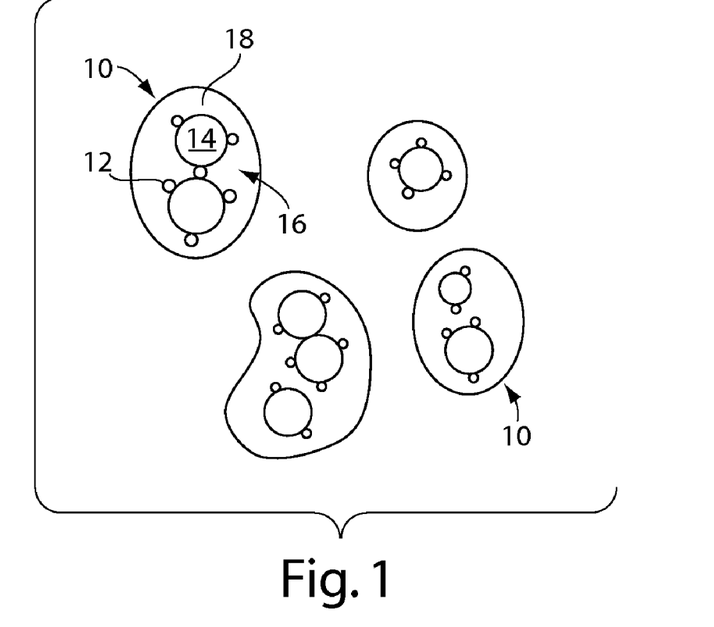
FIG. 1 shows coated composites according to one embodiment of the invention.

FIG. 1 schematically illustrates a plurality of composites 10 according to one embodiment of the invention. In the illustrative embodiment, the composites include one, or more, quantum dots 12 and one, or more, magnetic nanoparticles 14. The quantum dot(s) and magnetic nanoparticle(s) combine to form a core 16 which, at least, in part, is encapsulated by a shell 18.

The term "nanoparticle" is used herein as it is known in the art and typically refers to particles having a dimension of less of 100 nanometers. "Quantum dots", or "semiconductor nanocrystals", are a class of nanoparticles that can provide unique emission spectra dependent, in part, on the size of the specific particle. "Magnetic nanoparticles" are a class of nanoparticles that exhibit magnetic properties.

Quantum dots 12 may have any suitable semiconductor material composition. For example, quantum dots may be formed of Group II-VI semiconductors such as CdSe, CdTe, CdO, ZnO, ZnS, ZnSe, ZnTe, MgO, MgS, MgSe, MgTe, HgO, HgS, HgSe, HgTe, SrS, SrSe, SrTe, BaSe and BaTe. The quantum dots may also be formed of Group III-V compounds such as AlN, AlP, AlAs, AlSb, GaN, GaP, GaAs, GaSb, InN, InP, InAs, InSb, TiN, TiP, TiAs and TiSb. In some cases, the quantum dots may be formed of Group IV semiconductors such as silicon or germanium. It should also be understood that the quantum dots may comprise alloys or mixtures of any of the above-mentioned semiconductors. Other quantum dot compositions known to those of ordinary skill in the art may also be suitable. The specific composition is typically selected, in part, to provide the desired optical properties. In some embodiments, it may be preferred for the quantum dot to have a cadmium-based composition such as CdSe. It is also possible for composites of the invention to include quantum dots having different compositions.

The quantum dots generally have particle sizes of less than 100 nanometers. In some cases, the average particle size of the quantum dots in the composite is less than 20 nanometers; in other cases, the average particle size is less than 5 nanometers (e.g., about 3.5 nanometers). In some embodiments, the average particle size of the quantum dots is greater than 0.5 nanometer. As described further below, the quantum dots may be smaller than the magnetic nanoparticles. It should be understood that the composites may include quantum dots having different particle sizes which have different light emitting properties.

The average particle size may be determined using standard techniques, for example, by measuring the size of a representative number of particles using microscopy techniques (e.g., TEM).

The quantum dots are generally spherical in shape, though other shapes are also possible.

Individual composites typically include more than one quantum dot, as shown. That is, core 16 includes more than one quantum dot encapsulated, at least in part, by shell 18. However, it should be understood that, in some embodiments, the composites include a single quantum dot. As described further below, the ratio of quantum dots to magnetic particles within the composite may be controlled to provide desired properties.

Magnetic nanoparticles 14 may have any suitable composition. For example, the magnetic nanoparticles may comprise iron, cobalt and/or nickel, amongst other magnetic materials. In some cases, the magnetic material is in the form of a metal compound or alloy, such as iron oxide (e.g., $Fe_2O_3$, $Fe_3O_4$) or iron platinum (FePt). In other cases, the magnetic material may be a pure metal, such as cobalt or nickel. The composition of the magnetic nanoparticles is selected to provide desired magnetic properties. For example, the magnetic nanoparticles may be superparamagnetic at 5K and 300K. In some embodiments, it may be preferable to use $Fe_2O_3$ magnetic nanoparticles.

In some cases, the magnetic nanoparticles are not water soluble, but may be soluble in organic solvents. Such non-water soluble nanoparticles differ from water soluble nanoparticles used in certain conventional techniques.

The magnetic nanoparticles generally have particle sizes of less than 100 nanometers. In some cases, the average particle size of the magnetic nanoparticles in the composite is less than 20 nanometers (e.g., about 10 nanometers). In some embodiments, the average particle size of the magnetic nanoparticles is greater than 1.0 nanometer.

The magnetic nanoparticles are generally spherical in shape, though other shapes are also possible. One, or more than one (e.g., two or three), magnetic nanoparticles may be present within each composite.

The quantum dots are typically in contact with at least one of the magnetic nanoparticles within an individual composite. Oftentimes, more than one quantum dot is in contact with a magnetic nanoparticle. In some cases, a quantum dot may be in contact with more than one magnetic nanoparticle.

The contact results from attractive forces between the nanoparticles and quantum dots that arise during processing, as described further below. Typically, the contact is physical in nature and the magnetic nanoparticles and quantum dots are not chemically bound to one another.

As noted above, the composites include shell 18 that encapsulates, or partially encapsulates, the core. In some embodiments, it is preferable for the shell to encapsulate the majority of the surface area of the core. For example, the shell may encapsulate at least 75% of the surface area of the shell. In some cases, the shell may completely encapsulate the core.

In some embodiments, the shell is not chemically bound to the core (e.g., to the magnetic nanoparticles or quantum dots) and yet may contain the nanoparticle by encapsulation. Thus, the core and shell may be devoid of ionic bonds and/or covalent bonds between the two.

It may be preferred for the shell to be non-organic and may be formed of a silicon polymer such as silica. A "non-organic shell" is one that is not based on carbon and/or polymers of carbon, but nonetheless may include carbon atoms. It should also be understood that the shell may be organic and based on carbon and/or polymers of carbon.

In certain embodiments, the shell may be porous. For example, the shell may have pores on the mesoscale size. It should also be understood that the shell may be non-porous.

The shell has a thickness great enough to encapsulate the core to the extent desired. In some embodiments, the shell has an average thickness of less than 50 nanometers; and, in some embodiments, the shell has an average thickness of less than 25 nanometers (e.g., between 5 nanometers and 20 nanometers). The average shell thickness may be determined using standard techniques by measuring the thickness at a representative number of locations using microscopy techniques (e.g., TEM).

The composites (including the shell), of course, have a size greater than that of the magnetic nanoparticles and quantum dots. The composites can be referred to as "nanocomposites" or "nanocomposite structures". In some embodiments, the composites have a size of less than 200 nanometers. For example, the composites may be between 25 nanometers and 100 nanometers (e.g., 50 nanometers). Again, the particle size may be determined using standard microscopy techniques (e.g., TEM).

As noted above, the composites may include a desired ratio of the number of quantum dots to the number of magnetic particles. Typically, the ratio of quantum dots to magnetic particles is greater than 1. In some embodiments, the ratio may be between 1 and 4 (e.g., about 2). The ratio may be important in providing the desired optical and magnetic properties. For example, higher ratios may increase the fluorescent activity of the composites. The ratio may be controlled by processing parameters including the relative weight percentages of the quantum dots and magnetic particles used during processing, as described further below.

It should be understood that, in a collection of composites, not every composite will have the desired ratio. Some composites in the collection will have ratios above and below the desired ratio, though on average, the collection may have a desired ratio.

Typical weight percentages (based on the total weight of the composite, including shell) of the quantum dots in the composite may be between about 1% and about 5% (e.g., 3.5%). Typical weight percentages of the magnetic nanoparticles (based on the total weight of the composite, including shell) in the composites may be between about 1% and about 5% (e.g., 4%). The weight percentage of the shell (based on the total weight of the composite) may be, for example, greater than about 90% (e.g., 92.5%). Other components may also be present in the composites in minor amounts (e.g., less than 0.05%) including surfactants (e.g., IGEPAL CO-520).

In some embodiments, shell 18 (particularly when the shell is silica) can be functionalized or derivatized to include compounds, atoms, or materials that can alter or improve properties such as water solubility, water stability, photo-stability and biocompatibility. For example, the shell can include moieties such as polyethylene glycol (PEG) and other glycols. The composites, with and without PEG, have been shown to be non-toxic to living cells for extended periods, and it is believed that the composites are also non-toxic in vivo due, at least in part, to the isolation of the toxic core within the shell. The shell may also be linked to bioconjugators, such as avidin.

Figure 2:
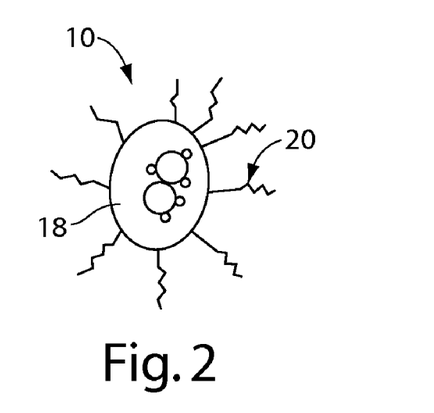
FIG. 2 shows a hydrophilic species associated with a shell of a composite according to one embodiment of the invention.

As shown in FIG. 2, a hydrophilic species 20 may be associated with the shell (e.g., a silica shell) to provide greater hydrophilicity to the composite. The hydrophilic species can be, for example, a polyethylene glycol (PEG) or a derivative of polyethylene glycol. Derivatives include, but are not limited to, functionalized PEGs, such as amine, thiol and carboxyl functionalized PEG. The hydrophilic species can be chemically bound to the shell or can be, for example, physically trapped by the shell material. Preferably, the hydrophilic species includes a portion that can be chemically bonded to the shell and a second portion that provides hydrophilicity and may extend outwardly from the surface of the shell.

Presence of these glycols can impart superior water solubility characteristics to the composites while being biocompatible and nontoxic and can, in some instances, provide for better dispersion of the nanoparticles in solution. For example, by integrating PEG into the shell (which may be silica), the composite may be rendered water soluble at pHs of less than 8.0 or less than or equal to 7.0. Thus, these composites may be water soluble at neutral or below neutral pHs and thus may be biocompatible and appropriate for use in biological fluids such as blood and in vivo. In some embodiments, the inclusion of PEG into the silica shell can enable the composites to remain in solution for extended time periods (e.g., greater than 6 hours).

The term "water soluble" is used herein as it is commonly used in the art to refer to the dispersion of a nanoparticle in an aqueous environment. "Water soluble" does not mean, for instance, that each material is dispersed at a molecular level. A nanoparticle can be composed of several different materials and still be "water soluble" as an integral particle.

In addition, the presence of PEG or related compounds in the silica shell can provide for a composite exhibiting a reduced propensity to adsorb protein, cells, and other biological materials. This means that, for example, when used in vivo, the composites can stay in solution for a longer period of time than do similar composites, thus allowing for increased circulation and improved deliverability to intended targets.

It should be understood that other suitable derivatives (e.g., compounds, atoms, or materials) may be attached to the shell to impart desired characteristics.

Figure 3:
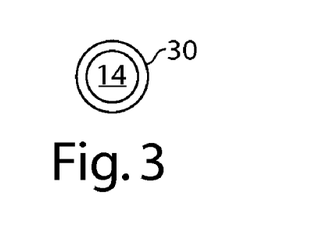
FIG. 3 shows a quantum dot including a passivation layer according to one embodiment of the invention.

In some embodiments, the quantum dots may include a passivation layer 30 as shown in FIG. 3. A "passivation" layer is a material associated with the surface of a quantum dot that serves to eliminate energy levels at the surface of the crystal that may act as traps for electrons and holes that degrade the luminescent properties of the quantum dot.

In some embodiments, the passivation layer may be formed of a material that is non-conductive and/or non-semi-conductive. For example, the passivation layer may be of a material that does not exhibit a higher band gap than a nanocrystal which it surrounds. In specific embodiments, the passivation layer may be non-ionic and non-metallic. A non-conductive material is a material that does not transport electrons when an electric potential is applied across the material.

The passivation layer can be comprised of, or consist essentially of, a compound exhibiting a nitrogen-containing functional group, such as an amine. The amine may be bound directly or indirectly to one or more silicon atoms such as those present in a silane or other silicon polymer. The silanes may include any additional functional group such as, for example, alkyl groups, hydroxyl groups, sulfur-containing groups, or nitrogen-containing groups. Compounds comprising the passivation layer may be of any size but typically have a molecular weight of less than about 500 or less than about 300. The preferred class of compounds are the amino silanes and in some embodiments, amino propyl trimethoxysilane (APS) can be used. The use of APS in quantum dots has been shown to provide passivation and to improve quantum yields to a level comparable to the improvements obtained by the use of higher band gap passivation layers such as those made of zinc sulfide (ZnS).

It should be understood that quantum dots do not include a passivating layer in all embodiments of the invention.

Any suitable conventional technique known in the art for forming magnetic nanoparticles and quantum dots may be used. For example, one suitable technique for forming the magnetic nanoparticles has been described in Hyeon et. al., *J. Am. Chem. Soc.*, 2001, 123, 12798, which is incorporated herein by reference. One suitable technique for preparing quantum dots has been described in Peng et. al., *J. Am. Chem. Soc.* 2001, 123, 183, which is incorporated herein by reference. Most conventional processes for forming quantum dots result in the quantum dots capped with a trioctyl phosphine oxide (TOPO) surfactant.

A reverse microemulsion process may be used to form the coated composites. A "reverse emulsion" or "aqueous in non-aqueous emulsion" is a dispersion of discrete areas of aqueous solvent (aqueous phase) within a non-aqueous solvent. The process may involve adding the separately formed magnetic nanoparticles and quantum dots to a reverse microemulsion. The magnetic nanoparticles and quantum dots may be added in controlled concentrations to effect the resulting ratio of quantum dots to magnetic nanoparticles in the composite.

The reverse microemulsion can be produced using a variety of non-polar solvents. Preferably, the non-polar solvent is a hydrocarbon and may be an aliphatic hydrocarbon and, in some cases, is a non-aromatic cyclic hydrocarbon such as cyclopentane, cyclohexane or cycloheptane.

In some embodiments, a surfactant (e.g., ionic or non-ionic) may be added to the reverse microemulsion. A "surfactant" is a material exhibiting amphiphilic properties and is used herein as it is commonly used in the art, e.g., for introducing hydrophobic species to hydrophilic environments.

Non-ionic surfactants include, for example, polyphenyl ethers, such as IGEPAL CO-520, while ionic surfactants include, for example, dioctyl sulfosuccinate sodium salt (AOT). As noted above, the quantum dots typically are capped with a trioctyl phosphine oxide (TOPO) surfactant. TOPO includes a hydrophilic end comprising phosphine oxide, while IGEPAL includes a hydrophilic end comprising polyoxyethylene (PEO). After introduction of the TOPO quantum dots into the reverse emulsion, the TOPO can be partially or completely exchanged for IGEPAL due, in part, to the much higher concentration of IGEPAL in the reverse emulsion. The IGEPAL also caps the magnetic nanoparticles. The quantum dots and magnetic nanoparticles, once capped with IGEPAL, are drawn into the aqueous areas of the micro-emulsion, thus providing an environment for the formation of the shell as described further below.

It should be understood that surfactants other than IGEPAL may be used and may be varied, in part, depending upon the quantum dot material, how the quantum dot is capped and the reverse emulsion that is used. Preferred surfactants include those that can be exchanged for TOPO, or other surfactants that are used to cap the quantum dot, and that also provide enough hydrophilicity to draw the core into aqueous areas of the micro-emulsion.

The quantum dots and magnetic nanoparticles (once capped with IGEPAL) are attracted to one another to form a core within the aqueous areas in the reverse emulsion. A sol-gel precursor, such as tetraethylorthosilicate (TEOS) can be polymerized using methods known to those skilled in the art, around the core to produce a silica shell. The polymerization reaction is allowed to proceed for time sufficient to obtain the desired silica shell thickness. A "precursor" is a substance that can be transformed into a second substance that exhibits different properties from the first. For example, a monomer is a polymer precursor if it can be transformed into a polymer.

The resulting nanostructure includes a core comprising quantum dots and magnetic nanoparticles and a shell of polymerized silica. In some cases, a passivation layer may be present (e.g., of an amino silane such as APS).

It should be understood that, when forming other shells (non-organic or organic), suitable precursors known in the art are used.

In some embodiments, the shell may be functionalized or derivatized, as described above, to improve biocompatibility, water solubility or other characteristics. For example, in some embodiments a PEG modified silica shell can be formed around a the composites. As described above, the quantum dots and magnetic nanoparticles may be introduced into the reverse micro-emulsion to form cores to be encapsulated. In another step, a base, such as ammonia ($NH_4OH$), including a glycol, such as polyethyleneglycol monomethylether (PEG-m), can be dissolved into the microemulsion. The PEG may be of any molecular weight, but it is preferably of a molecular weight of greater than 1,000 and less than 20,000 (e.g., between 5,000 and 10,000). A sol-gel precursor, such as TEOS, can then be added and the mixture can be stirred allowing the PEG to be incorporated into the forming silica shell. The resulting silica shell derivatized with PEG can provide for improved quantum yield, improved water solubility, improved biocompatibility in a reduced propensity to coagulate.

The amount of water (29.5% aqueous $NH_4OH$) in the reverse microemulsion can be varied based upon the specific reaction that is desired. For example, in some embodiments the amount of water in the reverse microemulsion is between 0.1 and 0.5 percent by volume. In some preferred embodiments, the amount of water is between 0.2 and 0.4 percent by volume and, in some embodiments, it has been found that quantum yield can be maximized when the amount of water in the reverse microemulsion is about 0.25 percent by volume.

The amount of sol-gel precursor added to the microemulsion can also affect the properties of the composites. For example, while an increase in the amount of sol-gel precursor does not appear to increase the shell thickness, an increase in the amount of sol-gel precursor does appear to improve this sphericity as well as the monodispersity of the composites. In some embodiments, quantum yield is also improved with higher concentrations of sol-gel precursor.

It should be understood that other processes may also be suitable for forming the composites of the present invention.

As noted above, the composites of the present invention may be used in a variety of applications including biological applications and medical applications. For example, the composites may be used in bio-imaging, labeling, magnetic resonance imagine (MRI) drug targeting and novel optical communications systems (e.g., photonic crystals), amongst other applications.

The following example is illustrative and not intended to be limiting.

EXAMPLE

This example illustrates production and characterization of coated composites of the present invention.

Magnetic $Fe_2O_3$ nanoparticles were prepared using a technique described in Hyeon et. al., *J. Am. Chem. Soc.*, 2001, 123, 12798. CdSe quantum dots were prepared using a technique described in Peng et. al., *J. Am. Chem. Soc.* 2001, 123, 183.

A polyoxyethylene (5) nonylphenyl ether (0.544 mmol Igepal CO-520, containing 50 mol % hydrophilic group) was well dispersed in cyclohexane (4.5 ml) by sonication to form a reverse microemulsion medium. 400 microliters of $Fe_2O_3$ solution (0.5 mg/1 ml of cyclohexane) and 160 microliters CdSe solution (1 mg/1 ml of cyclohexane) were added to the medium to form a mixture. The mixture was vortexed, and aqueous ammonia (29.4%, 40 microliter) was added to form transparent brown solution of reverse micelle microemulsion. Tetraethylorthosilicate, TEOS, (Aldrich, 30 microliters) was added to the reaction solution. Composite samples were collected after 8 hours and 48 hours of reaction time. The composites were collected by magnet and washed and redispersed in ethanol or deionized water.

Figure 4A:
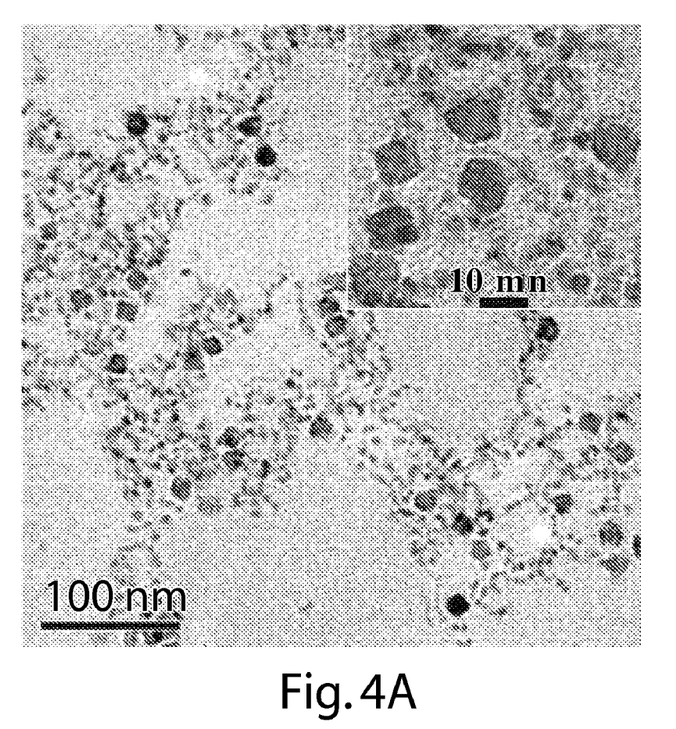
FIGS. 4A and 4B are transmission electron microscopy (TEM) images of composites described in the Example.
Figure 4B:
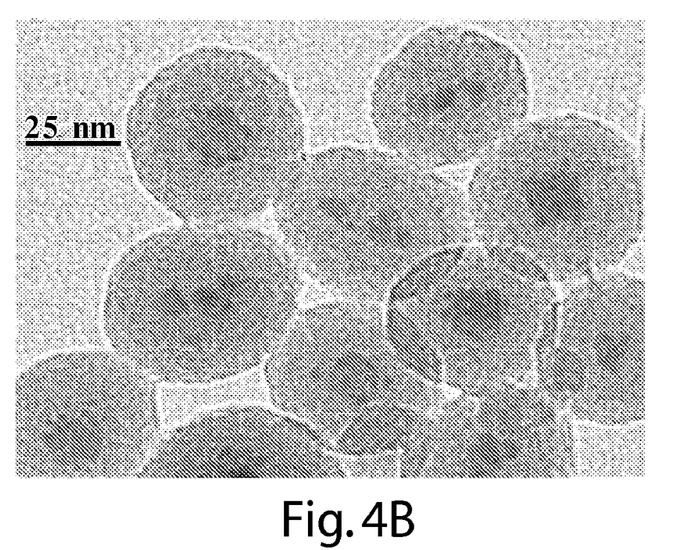

FIGS. 4A and 4B are transmission electron microscopy (TEM) images of the composites. The images show that the composites include silica shells around a core comprising $Fe_2O_3$ nanoparticles and CdSe quantum dots. EDX analysis of the region shown in FIG. 4B confirmed the presence of CdSe, $Fe_2O_3$ and silica. $N_2$ sorption isotherm of the composites indicated that the silica shells were non-porous.

Figure 5:
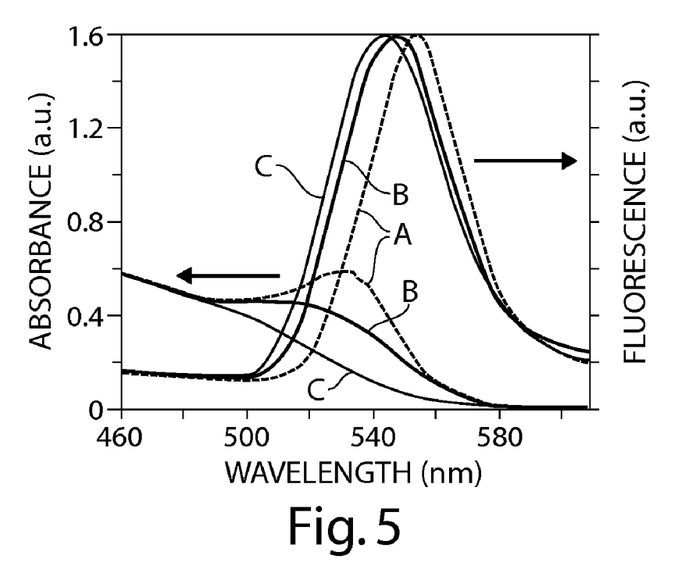
FIG. 5 is a UV-Vis and normalized fluorescence spectra of the bare CdSe particles, the composites after 8 hours reaction time, and the composites after 48 hours reaction time described in the Example.

Emission properties of the composites were measured and compared to properties of bare CdSe particles. FIG. 5 is a UV-Vis and normalized fluorescence spectra ($\lambda_{ex}$=365 nm) of the bare CdSe particles (line A), composites after 8 hours reaction time (line B) and composites after 48 hours reaction time (line C). Bare CdSe showed an absorption onset at 564 nm, an absorbance peak at 530 nm, and the exciton peak at 554 nm. As the silication reaction proceeded from 8 hours to 48 hours, the absorption peak shifted to shorter wavelength and became less pronounced. This blue shift can also be observed in fluorescence spectra; 7 nm for 8 hours; 10 nm for 48 hours; and the excitonic band became broader. The quantum yield (QY) of the emission was estimated to be 11.4% for the bare CdSe; 3.2% for 8 hours; and, 1.1% for 48 hours reacted; ethanol solubilized Rhodamine 6G, QY 94%, was used as a reference. It is believed the relatively weak fluorescence may be due to the thick silica shell.

Magnetic properties of the composites (coated with silica) were measured and compared to the properties of magnetic nanoparticles coated with silica. Magnetic characterization was performed using super conducting quantum interference devices (SQUID).

Figure 6A:
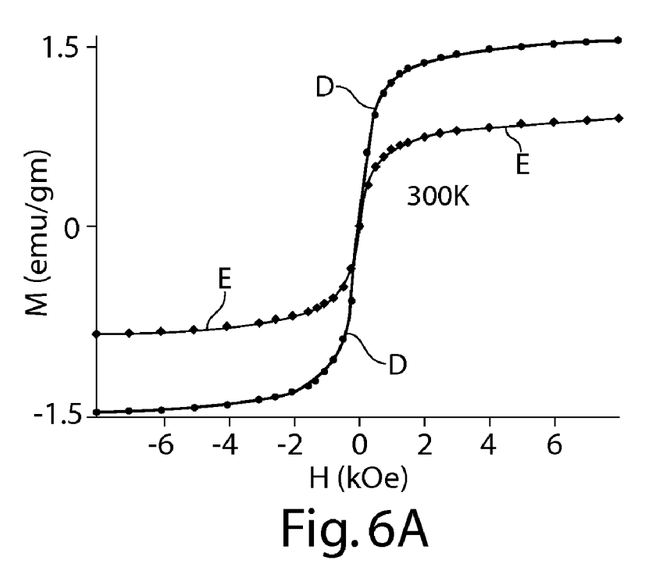
FIGS. 6A and 6B are field dependent magnetization plots at 300K and 5K for the magnetic nanoparticles coated with silica and the composites described in the Example.
Figure 6B:
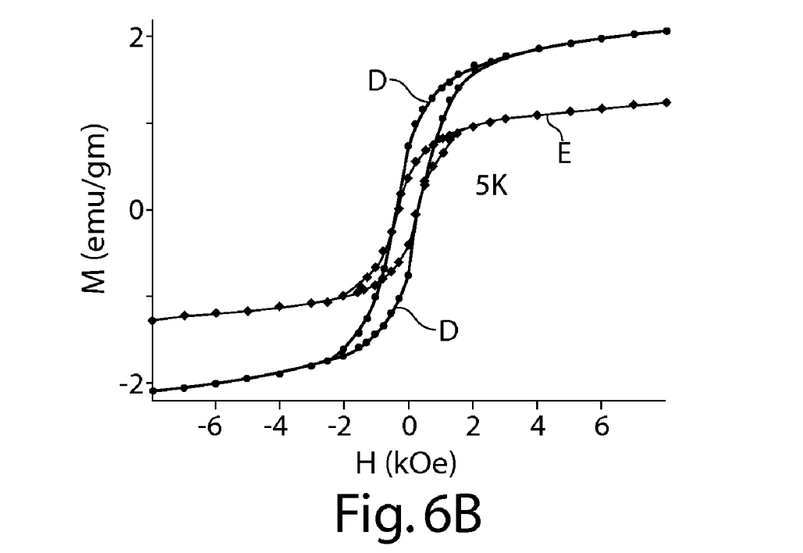

FIGS. 6A and 6B are field dependent magnetization plots showing that both magnetic nanoparticles coated with silica (Line D) and composites (Line E) were super paramagnetic at 300 K, and hysteric at 5 K. The magnetic nanoparticles coated with silica showed higher magnetization compared to the composites at 5 K and 300 K. These raw data were presented in emu per gram of sample. When normalized to the $\gamma$-Fe$_2$O$_3$ content in each sample, magnetization values in emu/g of $\gamma$-Fe$_2$O$_3$ were found to be similar between the magnetic nanoparticles coated with silica and the composites.

Figure 6C:
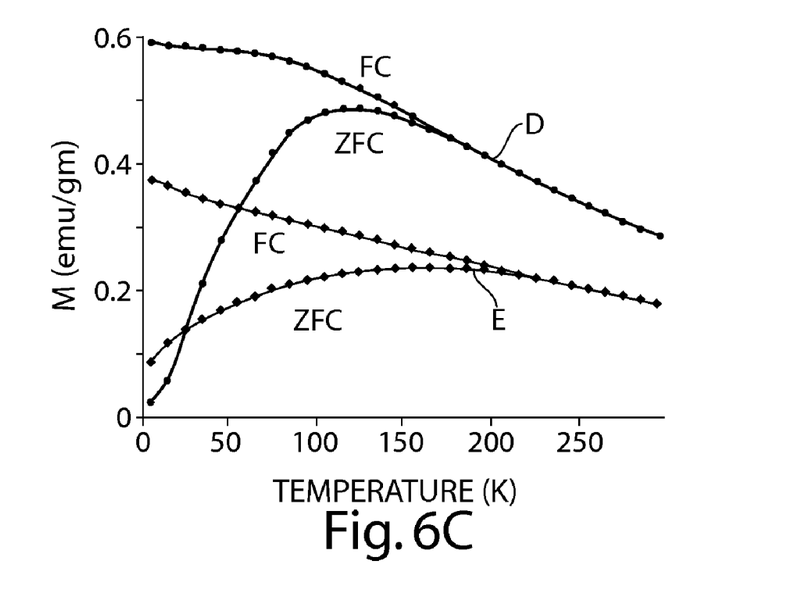
FIG. 6C is a temperature dependent magnetization plot at 100 Oe for the magnetic nanoparticles coated with silica and the composites described in the Example.

FIG. 6C shows the temperature dependence of magnetization at 100 Oe for the magnetic nanoparticles coated with silica (Line D) and composites (Line E). As shown, the coercivity values were also similar to each other at 5K. Zero-field-cooled (ZFC) and field-cooled (FC) magnetization were measured in an applied field of 100 Oe at temperatures between 5 and 300K. They exhibited typical behaviors of $\gamma$-Fe$_2$O$_3$ nanoparticles. The blocking temperature ($T_B$) were 125 for magnetic nanoparticles, and 165 for composites, respectively. These values were comparable to the $T_B$ of $\gamma$-Fe$_2$O$_3$ nanoparticles.

For uniaxial anisotropy, the superparamagnetic relaxation time is given by $\tau_s = \tau_o \exp(KV/k_B T)$, where $\tau_o$ is a constant on the order of $10^{-9}$ s, and V is the particle volume. For the magnetic nanoparticles coated with silica and composites, the magnetic anisotropy density (K) was $0.39 \times 10^5$ J/m$^3$ and $0.51 \times 10^5$ J/m$^3$, respectively, assuming a SQUID characteristic measuring time of 10 sec. The presence of the quantum dot(s) (CdSe) in the composite increased the effective magnetic anisotropy of the magnetic nanoparticles indicating that the quantum dots were closely connected to the magnetic nanoparticles.

In conclusion, this example establishes that composites of the present invention have unique optical and magnetic properties characteristic of the magnetic nanoparticles (Fe$_2$O$_3$) and quantum dots (CdSe) which form the composites.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc.

As used herein in the specification and in the claims, unless clearly indicated to the contrary, "or" should be understood to have the same meaning as "and/or" as defined above. For example, when separating items in a list, "or" and "and/or" each shall be interpreted as being inclusive, i.e., the inclusion of at least one, but also including more than one, of a number or list of elements, and, optionally, additional unlisted items. In general, the term "or" as used herein shall only be interpreted as indicating exclusive alternatives (i.e. "one or the other but not both") when preceded by terms of exclusivity, such as "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composite structure comprising:
   a core comprising at least two quantum dots and at least one magnetic nanoparticle associated with the at least two quantum dots, wherein the ratio of quantum dots to magnetic nanoparticles is greater than 1; and a shell comprising silica at least partially encapsulating the core.

2. The composite structure of claim 1, wherein the shell further comprises polyethylene glycol or a derivative thereof.

3. The composite structure of claim 1, wherein the structure is water soluble.

4. The composite structure of claim 1, wherein at least one quantum dot further comprises a passivating layer formed on a surface of the quantum dot.

5. The composite structure of claim 1, comprising a plurality of magnetic nanoparticles.

6. The composite structure of claim 1, wherein the quantum dot and the magnetic nanoparticle contact each other.

7. The composite structure of claim 1, wherein the magnetic nanoparticle comprises $Fe_2O_3$ and at least one quantum dot comprises CdSe.

8. The composite structure of claim 1, wherein the magnetic nanoparticle is water insoluble.

9. A method of making a composite structure, the method comprising:
   introducing magnetic nanoparticles and quantum dots to an aqueous-in-nonaqueous emulsion;
   contacting the magnetic nanoparticles and quantum dots with a surfactant;
   forming a core comprising at least one magnetic nanoparticle and at least two quantum dots in an aqueous phase of the emulsion, wherein the ratio of quantum dots to magnetic nanoparticles in the core is greater than 1;
   introducing a shell precursor to the emulsion; and
   polymerizing the precursor to form a shell that at least partially encapsulates the core to form a composite structure.

10. The method of claim 9, wherein the precursor is a non-organic shell precursor and the precursor is polymerized to form a non-organic shell.

11. The method of claim 9, wherein the precursor is a silica precursor and the precursor is polymerized to form a silica shell.

12. The method of claim 9, wherein the magnetic nanoparticles and quantum dots are capped with the surfactant.

13. The method of claim 9 further comprising introducing a polyethylene glycol, or a derivative thereof, to the emulsion.

14. The method of claim 13, wherein the shell comprises polyethylene glycol, or a derivative thereof.

15. The method of claim 9, wherein the structure is water soluble.

16. The method of claim 9, wherein the core comprises a plurality of quantum dots.

17. The method of claim 9, wherein the core comprises a plurality of magnetic nanopartieles.

18. The method of claim 9, wherein the surfactant is IGEPAL.

* * * * *

UNITED STATES PATENT AND TRADEMARK OFFICE
CERTIFICATE OF CORRECTION

PATENT NO. : 7,534,489 B2  Page 1 of 1
APPLICATION NO. : 10/950194
DATED : May 19, 2009
INVENTOR(S) : Jackie Y. Ying et al.

It is certified that error appears in the above-identified patent and that said Letters Patent is hereby corrected as shown below:

Column 12, Claim 17, line 24, the word "nanopartieles" should be "nanoparticles".

Signed and Sealed this

Fourteenth Day of July, 2009

JOHN DOLL
*Acting Director of the United States Patent and Trademark Office*